US012667410B2

(12) United States Patent
Nagtegaal et al.

(10) Patent No.: US 12,667,410 B2
(45) Date of Patent: Jun. 30, 2026

(54) ELECTROSURGICAL DEVICE

(71) Applicant: GYRUS ACMI, INC, Westborough, MA (US)

(72) Inventors: Marno Nagtegaal, Cardiff (GB); Matthew Davidge, Cardiff (GB)

(73) Assignee: GYRUS ACMI, INC, Westborough, MA (US)

( * ) Notice: Subject to any disclaimer, the term of this patent is extended or adjusted under 35 U.S.C. 154(b) by 778 days.

(21) Appl. No.: 17/671,044

(22) Filed: Feb. 14, 2022

(65) Prior Publication Data

US 2022/0273356 A1     Sep. 1, 2022

(30) Foreign Application Priority Data

Mar. 1, 2021    (GB) ..................................... 2102893

(51) Int. Cl.
| | |
|---|---|
| *A61B 18/14* | (2006.01) |
| *B23K 26/362* | (2014.01) |
| *C23C 4/10* | (2016.01) |
| *A61B 18/00* | (2006.01) |

(52) U.S. Cl.
CPC ........ *A61B 18/1442* (2013.01); *B23K 26/362* (2013.01); *C23C 4/10* (2013.01); *A61B 2018/00083* (2013.01); *A61B 2018/00404* (2013.01); *A61B 2018/00589* (2013.01); *A61B 2018/0063* (2013.01)

(58) Field of Classification Search
CPC ...... A61B 18/1442; A61B 2018/00083; A61B 2018/00404; A61B 2018/00589; A61B 2018/0063; B23K 26/362; C23C 4/10
See application file for complete search history.

(56) References Cited

U.S. PATENT DOCUMENTS

| | | | | |
|---|---|---|---|---|
| 6,106,523 A | * | 8/2000 | Morris ................... | A61B 18/14 606/49 |
| 2009/0182327 A1 | | 7/2009 | Unger | |
| 2013/0226177 A1 | * | 8/2013 | Brandt ............... | A61B 18/1445 606/49 |

(Continued)

FOREIGN PATENT DOCUMENTS

| | | |
|---|---|---|
| GB | 2534147 B | 11/2018 |
| GB | 2553386 B | 11/2018 |

OTHER PUBLICATIONS

Dec. 2, 2021 Search Report issued in Great Britain Patent Application No. 2102893.1.

(Continued)

*Primary Examiner* — Michael F Peffley
*Assistant Examiner* — Bo Ouyang
(74) *Attorney, Agent, or Firm* — Schwegman Lundberg & Woessner, P.A.

(57) ABSTRACT

An electrode for the electrosurgical end effector of a surgical instrument is manufactured by laser etching or roughening an area of the electrode's surface. This provides an area to which an insulating stop may be attached. Beneficially, the roughened area provides a good bond between the insulating stop and the electrode, allowing a greater potential use-life for the surgical instrument. Compared to conventional methods, using a laser reduces costs, increases manufacturing flexibility and allows precise control over the creation of the roughened area.

12 Claims, 4 Drawing Sheets

(56)                    References Cited

U.S. PATENT DOCUMENTS

| 2016/0058497 | A1* | 3/2016 | Brandt ................. B29C 70/683 |
| | | | 264/135 |
| 2017/0196636 | A1 | 7/2017 | Mccullough, Jr. et al. |
| 2018/0056077 | A1* | 3/2018 | Dadashian ........... A61N 1/3752 |
| 2019/0247111 | A1 | 8/2019 | Dycus et al. |
| 2022/0387068 | A1 | 12/2022 | Witt et al. |

OTHER PUBLICATIONS

Feb. 4, 2025 Examination Report issued in Great Britain Patent Application No. 2102893.1.
Sep. 11, 2024 Examination Report issued in Great Britain Patent Application No. 2102893.1.
Nov. 22, 2024 Examination Report issued in Great Britain Patent Application No. GB2102893.1.
Apr. 11, 2025 Examination Report issued in Great Britain Patent Application No. 2102893.1.

* cited by examiner

ELECTROSURGICAL DEVICE

TECHNICAL FIELD

Embodiments of the present invention described herein relate to an electrosurgical device, and in particular an electrosurgical forceps device for vessel sealing. A laser is used to roughen the surface of an electrode of an electro-surgical end effector before attaching insulating stops.

BACKGROUND TO THE INVENTION AND PRIOR ART

Normally, vessel sealing devices are equipped with insulating stops along the length of one of the electrodes. So as to ensure a good bond between the electrode and the insulating stop, the electrode may have a stamped recess to which the insulating stop is attached. Alternatively, an area of the electrode may be chemically etched or bead/sand blasted before the insulating stop is attached.

Each of these methods has negative attributes in terms of adhesion quality (between the insulating stop and the electrode), flexibility and manufacturing cost. For example, where a mask is used during manufacture, as in chemical etching and bead/sand blasting, adapting the manufacturing process can be difficult, requiring a new mask to be produced. This adds costs and reduces the ability for a manufacturer to change the design in a timely fashion. The same is true where a recess is stamped, with a different tool required for a different shape or size.

One prior art arrangement, as described in GB 2553386 B, describes end-effector assemblies for an electrosurgical instrument. An upper jaw and a lower jaw are arranged to open and close, supplying an electrosurgical signal for the sealing or coagulation of tissue. Electrically conductive stop members are disposed on one or more of a pair of sealing electrodes, preventing the electrodes from shorting when the jaws close.

Another prior art arrangement, as shown in GB2534147, describes the use of stop members on a jaw for an electrosurgical instrument. Shims may be located on the inner faces of the jaw to act as electrodes during use. A plurality of cut outs are spaced along the shim, allowing a flowable plastic material such as polypropylene to be injected and fill the cut outs, protruding above the shim and forming stop members.

So as to improve on the prior art, the present disclosure seeks to provide an improved method of manufacture for an electrode which is simpler to perform with fewer steps involved.

SUMMARY OF THE INVENTION

Embodiments of the present invention provide an improved method for attaching an insulating stop to an electrode. The electrode surface is roughened in the position where the insulating stop is to be applied, and then the insulating stop is adhered to the roughened surface. In order to generate the roughened area a laser is used to locally etch or roughen the area of the electrode where the insulating stop is to be attached prior to the insulating stop being bonded thereto. Beneficially, this can allow an improved bond between the electrode and the insulating stop and increase the potential life of the electrosurgical instrument. Using laser etching provides for a spatially accurate and non-contact method of generating the roughened area on the electrode surface, which is readily controllable and capable of integration into the electrode production process. In addition, roughening the surface of the electrode to permit good adhesion of the stops is preferable to arrangements such as in the prior art where holes are formed in the electrode surface to allow stop securing portions to be located underneath the electrode, as the electrode integrity is not altered via the forming of holes, and the manufacturing process is easier.

The electrode may be manufactured for use in an electrosurgical instrument that allows vessel sealing. The insulating stops prevent an electrode on an upper jaw from contacting an electrode on a lower jaw, preventing a short circuit and ensuring spacing between the electrodes is maintained.

Accordingly, a method of manufacture of an electrode for an electrosurgical end effector comprises applying a surface coating to a shim; laser etching a first area of the shim; and attaching an insulating stop to the shim at the first area.

Advantageously, laser etching a surface of the shim improves the bond between the shim and the insulating stop. It also allows a cheaper, faster and more efficient means of manufacture than presently known methods. For example, where different sized areas are required, or different sized insulating stops are required, no tooling changes are necessary. This technique can also be performed at any stage during the manufacture of the shim, whereas conventional techniques (such as stamping a recess) may need to be performed in the first stage of manufacture, due to tool requirements.

In one embodiment, the surface coating is titanium nitride, TiN. Beneficially, titanium nitride is a non-toxic material.

In another embodiment, laser etching the first area of the shim comprises locally removing an area of the surface coating.

In one example, laser etching a first area of the shim comprises roughening a surface of the first area of the shim. Advantageously, a rough surface improves the bond between the insulating stop and the shim.

In another example, the insulating dot is a ceramic dot.

In a further example, the insulating stop is attached to the shim through a high velocity oxygen fuel coating, HVOF.

Further, in one example, the electrode forms part of a vessel sealing device. In another example, the shim includes a longitudinal groove, capable of receiving a blade.

In an example, laser etching a first area of the shim further comprises laser etching a plurality of areas of the shim; and attaching an insulating stop to the shim at the first area comprises attaching a plurality of insulating stops to the plurality of areas of the electrode. Applying multiple insulating stops to the shim ensures that shorting will not occur at any point of the shim. In a further example, the plurality of insulating stops are disposed adjacent to the longitudinal groove.

Another example comprises an electrosurgical end effector for an electrosurgical instrument, comprising: an upper jaw; a lower jaw attached to the upper jaw in a pivotable manner; a first shim attached to inner face of the upper jaw; a second shim attached to the inner face of the lower jaw, wherein the first shim or the second shim are manufactured according to the described examples.

In an example, when the jaws are closed, the insulating stops maintain a separation distance between the upper and lower shims. Beneficially, this prevents shorting of the shims.

In a final example, an electrosurgical radio frequency signal is applied to the first shim and the second shim, such that when the jaws are closed around tissue, the signal coagulates or seals tissue.

BRIEF DESCRIPTION OF THE DRAWINGS

Embodiments of the invention will now be described by way of example only and with reference to the accompanying drawings, wherein like reference numerals refer to like parts, and wherein.

DESCRIPTION OF THE EMBODIMENTS

Figure 1:
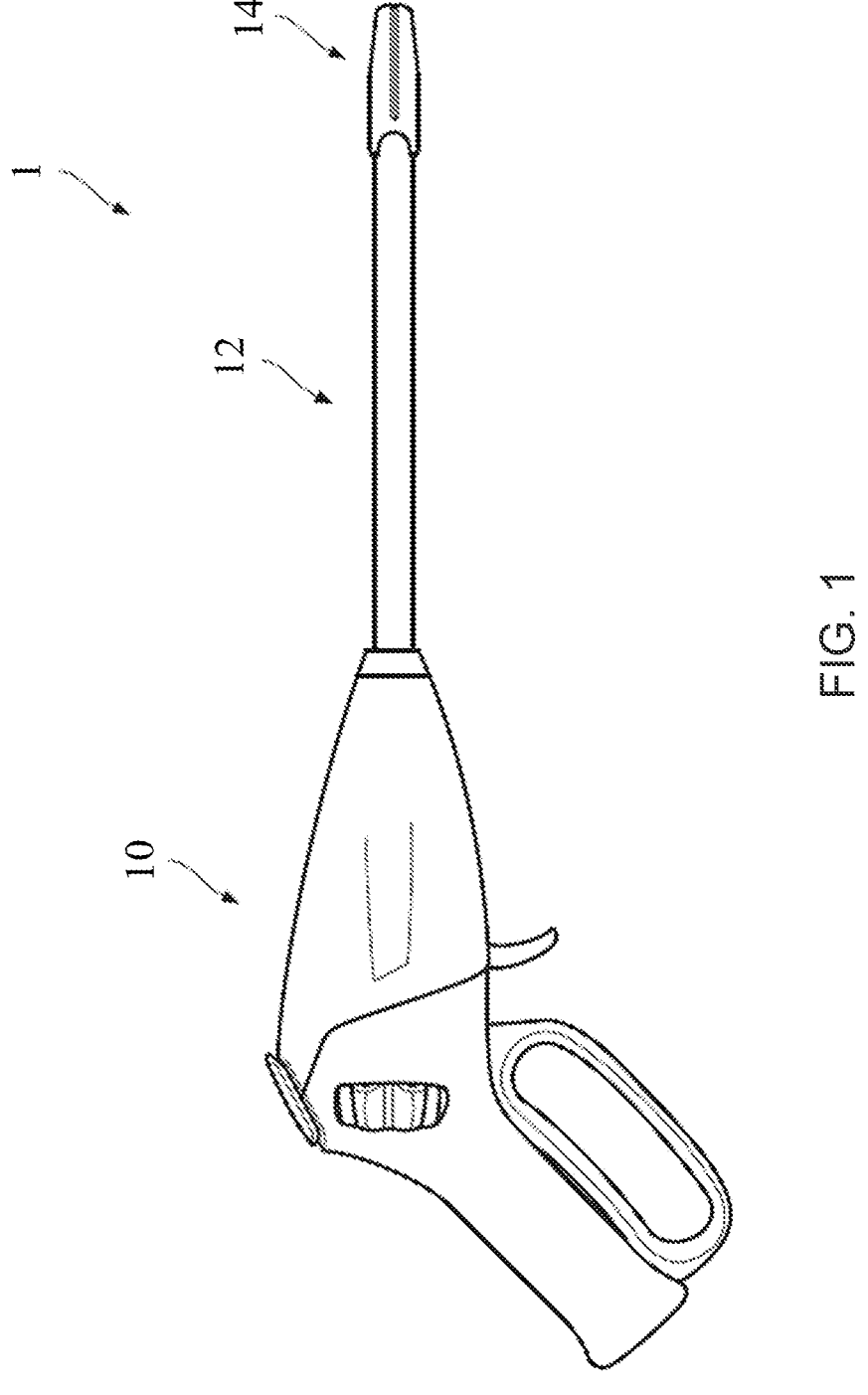
FIG. 1 is a side view of an electrosurgical instrument according to an embodiment of the present invention.

Referring to the drawings, FIG. 1 shows an electrosurgical instrument 1 according to an example of the present invention. The instrument 1 includes a proximal handle portion 10, an outer shaft 12 extending in a distal direction away from the proximal handle portion, and a distal end effector assembly 14 mounted on a distal end of the outer shaft. The end effector assembly 14 may by way of example be a set of opposed jaws arranged to open and close, and comprising one or more electrodes arranged on or as the inner opposed surfaces of the jaws and which in use have connections to receive an electrosurgical radio frequency (RF) signal for the sealing or coagulation of tissue. The jaws are further provided with a slot or other opening within the inner opposed surfaces through which a mechanical cutting blade or the like may protrude, when activated by the user. In use, the handle 10 is activated by the user in a first manner to clamp tissue between the jaws 14, and in a second manner to supply the RF current to the electrodes in order to coagulate the tissue. The jaws 14 may be curved so that the active elements of the instrument 1 are always in view. This is important in vessel sealing devices that are used to operate on regions of the body that obscure the user's vision of the device during use. The handle 10 may be activated by the user in a third manner to cause the blade to protrude between the jaws 14, thereby cutting the tissue clamped between. Once the required cutting and sealing has been completed, the user can release the tissue from the jaws 14. Although here an endoscopic tool is shown, the end effector is also suitable for use with traditional open surgery tools.

Figure 2:
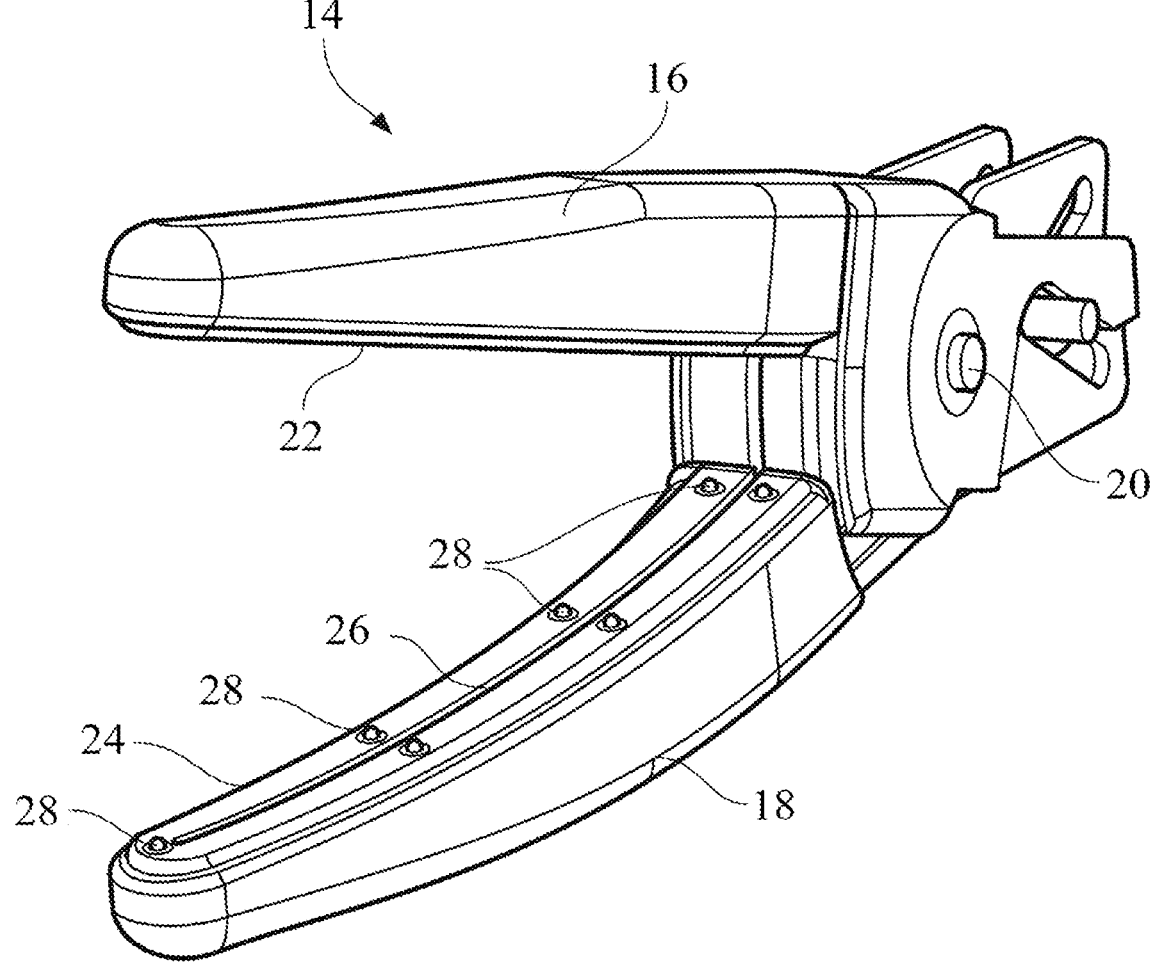
FIG. 2 is a schematic perspective view of an example end effector according to an embodiment of the present invention.

FIG. 2, shows an example end effector assembly 14, with stop members 28 disposed on one or both of the sealing electrodes. End effector 14 comprises an upper jaw 16 pivotably connected to a lower jaw 18 about a pivot 20. A shim 22 is present on the inward face of the upper jaw 16, while a shim 24 is present on the inward face of the lower jaw 18. When the jaws 16 and 18 pivot into their closed position, the shims 22 and 24 come into close proximity with one another, in order to grasp tissue (not shown) therebetween. The shims act as electrodes. The upper shim 22 has a longitudinal groove (not visible in FIG. 2) running the length thereof. The lower shim 24 has a corresponding longitudinal groove 26. The grooves in the shims 22 and 24 accommodate the longitudinal movement of a cutting blade (not shown).

The lower shim 24 is provided with a plurality of stop members 28, disposed along the length of the shim 24 and situated on either side of the groove 26. When the jaws 16 and 18 are moved to their closed position, the stop members contact the upper shim 22 maintaining a separation between the upper and lower shims 22 and 24. In use, a coagulating electrosurgical voltage is supplied between the shims 22 and 24, and the separation of the shims ensures effective sealing of tissue grasped between the jaw members 16 and 18. Electrical shorting of the shims is prevented, as the stop members are constructed of an insulating material. For example, they may be constructed of ceramic.

Figure 3:
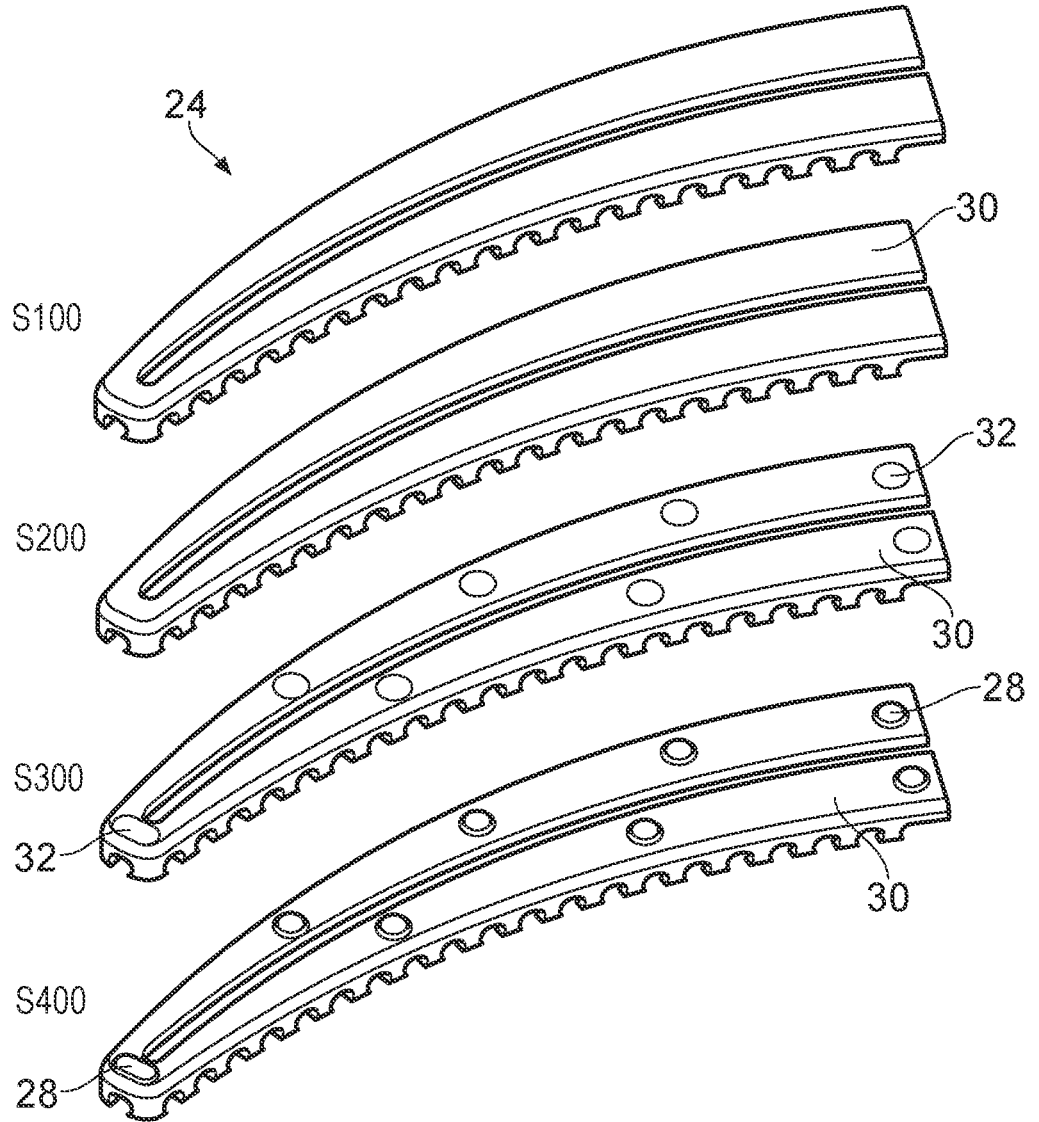
FIG. 3 is an overview of the manufacturing process of a shim according to an embodiment of the present invention.

As described in the background, conventional methods of attaching an insulating stop to the end effector assembly can result in poor adhesion, manufacturing complexity and high costs. Therefore the method of manufacture for a shim set out in FIG. 3 aims to improve on these attributes. FIG. 3 shows four steps (S100-S400) of a manufacturing process of a shim 24.

The shim 24 shown in FIG. 3 has a curve to one side. This allows the operator to clearly see the active element of the end effector. However the shim need not be curved Step S100 shows a shim 24. This shim may have been formed by stamping, machining, etching, folding or by a casting process.

In step S200, a surface coating 30 is applied to the shim 24. The surface coating may be a layer of Titanium Nitride (TiN). Beneficially, TiN is non-toxic.

In step S300, a laser is used to locally roughen or etch an area 32 of the surface coating 30. This creates a roughened area 32. The laser may not fully remove the surface coating 30, but may instead simply roughen the surface coating in the area 32. Alternatively, the laser etching may remove the surface coating 30 in the area 32, exposing the material underneath. This material may then be further roughened by the laser etching process, or may be rough by virtue of the material chosen. No mask is required at this stage, beneficially allowing a more flexible manufacturing process, with changes in design easily made without any additional tooling modifications. Multiple areas of the shim 24 may be etched by the laser, creating multiple roughened areas 32.

The use of laser etching allows multiple roughened areas 32 of different sizes to be created without the need for different size masks. For example, a roughened area 32 located at the distal end of the shim 24 may be a different shape to the roughened areas 32 located along the length of the shim 24. Using a laser in this way can reduce costs compared to stamping, sand blasting or chemical etching the electrode. It is also faster and can be done at any point during the electrode manufacture.

In step S400, insulating stops 28 are attached to the shim at the roughened areas 32 that have been etched by the laser. These insulating stops 28 may be constructed of ceramic. The insulating stops 28 may be attached to the shim using a High Velocity Oxygen Fuel coating (HVOF).

Figure 4A:
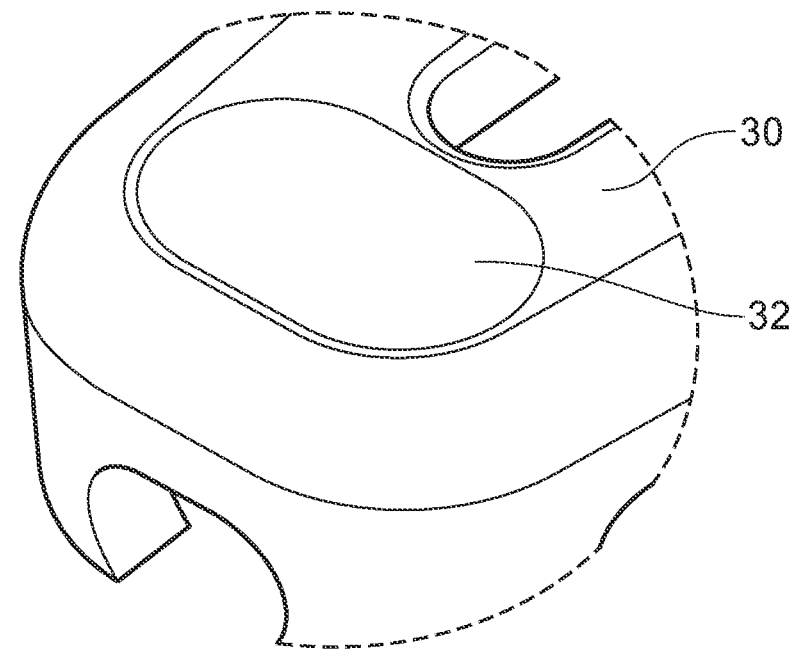
FIG. 4a is a view of the distal end of a shim according to an embodiment of the present invention.
Figure 4B:
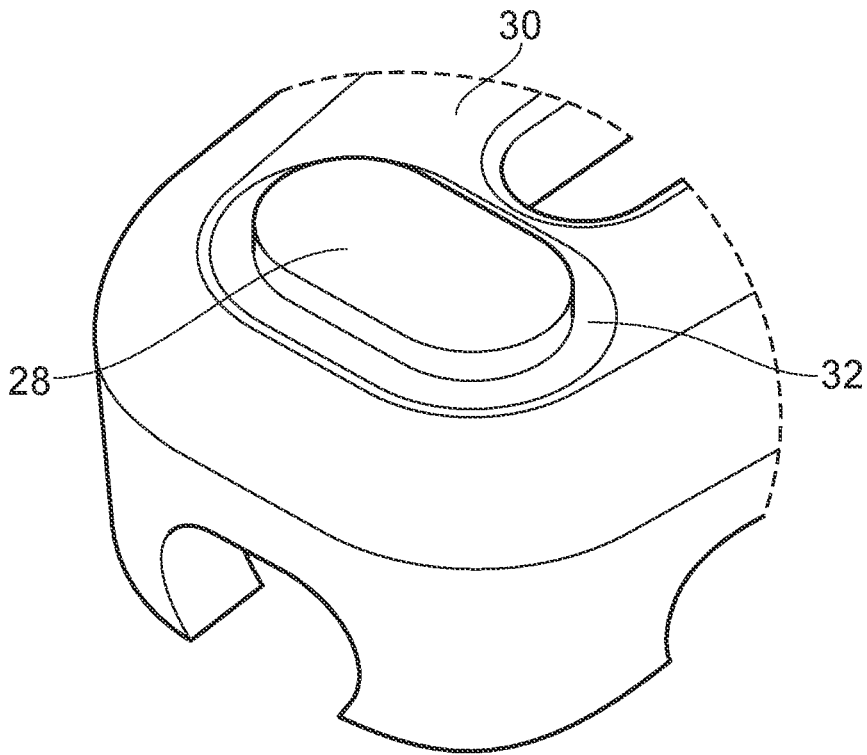
FIG. 4b is a view of the distal end of a shim, including an insulating stop, according to an embodiment of the present invention.

FIG. 4a shows the distal end of the shim 24, including an area 32 roughened by laser etching. FIG. 4b shows the distal end of the shim 24, where an insulating stop 28 is attached to the shim at the roughened area 32. The insulating stop 28 may be smaller than the roughened area 32, allowing easier placement of the insulating stop 28.

Whilst the above figures and accompanying description have described attaching an insulating stop 28 to a lower shim 24 of the electrosurgical device, it is clear that the insulating stops may be attached to the lower shim 24, the upper shim 22, or both the lower shim 24 and the upper shim 22.

Various modifications whether by way of addition, deletion, or substitution of features may be made to above described embodiment to provide further embodiments, any and all of which are intended to be encompassed by the appended claims.

The invention claimed is:

1. A method of manufacture of an electrode for an electrosurgical end effector, the method comprising:
   applying a surface coating to a shim;
   laser etching a first area of the shim, wherein laser etching the first area of the shim is performed without using a mask; and
   attaching an insulating stop to the shim at the first area, wherein the insulating stop is attached to the shim through a high velocity oxygen fuel coating, HVOF.

2. The method of manufacture according to claim 1, where the surface coating is titanium nitride, TiN.

3. The method of manufacture according to claim 1, wherein laser etching the first area of the shim comprises locally removing an area of the surface coating.

4. The method of manufacture according to claim 1, wherein laser etching a first area of the shim comprises roughening a surface of the first area of the shim.

5. The method of manufacture according to claim 1, wherein the insulating stop is a ceramic dot.

6. The method of manufacture according to claim 1, wherein the shim forms part of a vessel sealing device.

7. The method of manufacture according to claim 1, where the shim includes a longitudinal groove, capable of receiving a blade.

8. The method of manufacture according to claim 7, wherein:
   laser etching a first area of the shim further comprises laser etching a plurality of areas of the shim; and
   attaching an insulating stop to the shim at the first area comprises attaching a plurality of insulating stops to the plurality of areas of the electrode.

9. The method of manufacture according to claim 8, wherein the plurality of insulating stops are disposed adjacent to the longitudinal groove.

10. An electrosurgical end effector for an electrosurgical instrument, comprising:
    an upper jaw;
    a lower jaw attached to the upper jaw in a pivotable manner;
    a first electrode attached to inner face of the upper jaw; and
    a second electrode attached to the inner face of the lower jaw, wherein the first electrode or the second electrode are manufactured according to the method of any preceding claim.

11. The electrosurgical end effector according to claim 10, wherein when the jaws are closed, the insulating stops maintain a separation distance between the upper and lower electrodes.

12. The electrosurgical end effector according to claim 10, wherein an electrosurgical radio frequency signal is applied to the first electrode and the second electrode, such that when the jaws are closed around tissue, the signal coagulates or seals tissue.

* * * * *